(12) United States Patent
Hiraiwa et al.

(10) Patent No.: US 7,964,073 B2
(45) Date of Patent: Jun. 21, 2011

(54) AIR FUEL RATIO DETECTION APPARATUS

(75) Inventors: Masamichi Hiraiwa, Aichi (JP); Takeshi Kawai, Aichi (JP); Satoshi Teramoto, Aichi (JP); Shigeki Mori, Aichi (JP); Hiroshi Inagaki, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1153 days.

(21) Appl. No.: 11/604,218

(22) Filed: Nov. 27, 2006

(65) Prior Publication Data

US 2007/0119437 A1 May 31, 2007

(30) Foreign Application Priority Data

Nov. 28, 2005 (JP) ................................ 2005-342937

(51) Int. Cl.
*G01N 27/419* (2006.01)
(52) U.S. Cl. ............... 204/425; 204/424; 205/784.5; 73/23.31; 73/23.32
(58) Field of Classification Search .............. 204/406, 204/424–429; 205/783.5–785, 781; 73/23.31–23.32; 123/672–704
See application file for complete search history.

(56) References Cited

U.S. PATENT DOCUMENTS

| | | | | |
|---|---|---|---|---|
| 5,172,677 A | * | 12/1992 | Suzuki | 123/688 |
| 5,391,284 A | * | 2/1995 | Hotzel | 204/425 |
| 5,758,310 A | | 5/1998 | Kato | |
| 5,895,564 A | * | 4/1999 | Miyata et al. | 205/784.5 |
| 5,974,857 A | * | 11/1999 | Yamashita et al. | 73/23.32 |
| 6,332,966 B1 | * | 12/2001 | Sakai et al. | 204/425 |

FOREIGN PATENT DOCUMENTS

| | | |
|---|---|---|
| DE | 100 31 474 A1 | 4/2001 |
| EP | 0507149 A1 | 10/1992 |
| EP | 0833148 A2 | 4/1998 |
| JP | 4-313056 A | 11/1992 |
| JP | 9-170997 A | 6/1997 |
| JP | 10-104195 A | 4/1998 |
| JP | 2001-241347 A | 9/2001 |
| JP | 2004-69547 A | 3/2004 |

OTHER PUBLICATIONS

Non-Final Office Action, dated Apr. 1, 2010 (in U.S. Appl. No. 11/518,945).
Final Office Action, dated Jul. 12, 2010 (in U.S. Appl. No. 11/518,945).

* cited by examiner

*Primary Examiner* — Nam X Nguyen
*Assistant Examiner* — Bach T Dinh
(74) *Attorney, Agent, or Firm* — Sughrue Mion, PLLC

(57) ABSTRACT

Using a gas detection voltage Vs output from a terminal CU, a determination is made at to whether, after startup of an air-fuel ratio detection apparatus (1), a full-range air-fuel ratio sensor (10) has reached a semi-activated state in which a determination can be made as to whether the air-fuel ratio is on the rich or lean side based on a change in a gas detection signal Vic. After determining that the sensor has reached the semi-activated state, the signal Vic is compared with a threshold to determine whether the air-fuel ratio is on the rich or lean side. In the apparatus (1), the potential difference between an outer pump electrode of a pump cell (14) and a reference electrode of an oxygen concentration measurement cell (24) is obtained via a first differential amplification circuit (53) as the gas detection signal Vic, the signal Vic being highly responsive to a change in air-fuel ratio of exhaust gas.

3 Claims, 4 Drawing Sheets

AIR FUEL RATIO DETECTION APPARATUS

BACKGROUND OF THE INVENTION

1. Field of the Invention

The present invention relates to an air-fuel ratio detection apparatus for detecting, over a wide range, the air-fuel ratio of exhaust gas discharged from combustion equipment such as an internal combustion engine. More particularly, the present invention relates to an air-fuel ratio detection apparatus which enables accurate and fast air-fuel-ratio feedback control of combustion equipment after startup of the air-fuel ratio detection apparatus.

2. Description of the Related Art

For air-fuel ratio control of an internal combustion engine, an air-fuel ratio detection apparatus is known including a gas sensor for detecting the air-fuel ratio of exhaust gas discharged from an internal combustion engine. Known gas sensors for such a purpose include a sensor (λ sensor) that outputs one of two levels in accordance with the concentration of oxygen in exhaust gas (in accordance with whether the air-fuel ratio is rich or lean), and a sensor (called a full range air-fuel-ratio sensor, a linear air-fuel-ratio sensor, or the like; hereinafter also referred to as a "linear sensor") that outputs a sensing output over a wide oxygen concentration (air-fuel ratio) range while maintaining linearity. In recent years, in order to cope with strengthened emission controls which require a reduction in the emission of hazardous gas, demands have arisen to control the air-fuel ratio of an air-fuel mixture supplied to an internal combustion engine over a wide range. In view of this, a technique has been embodied in which a linear sensor is employed in place of a λ sensor, and air-fuel-ratio feedback control is performed on the basis of an output from the linear sensor.

Incidentally, a gas sensor of any of the above-described types mainly employs a structure in which a pair of electrodes are provided on opposite surfaces of a solid electrolyte to thereby form a cell. The gas sensor detects oxygen concentration (air-fuel ratio) by an electromotive force generated due to a difference in oxygen concentration between atmospheres to which opposite surfaces of the solid electrolyte are exposed, or by movement of oxygen ions via the solid electrolyte when current flows between the electrodes. These phenomena do not occur unless the solid electrolyte is heated to a certain temperature or higher and brought into a so-called active state. Therefore, consideration has been given to providing a heater in an air-fuel ratio detection apparatus so as to heat a gas sensor in order to quickly activate the same, and to thereby rapidly perform air-fuel-ratio feedback control on the basis of the output of the gas sensor after startup of an internal combustion engine.

However, a linear sensor having recently been put into practice requires a very long time of ten seconds to several tens of seconds before its cell is sufficiently activated and the sensor generates a stable output as a linear sensor, even when the linear sensor is heated by means of a heater. In order to overcome this drawback, an air-fuel-ratio detection apparatus as disclosed in Patent Documents 1 and 2 has been proposed in which such a linear sensor is used, and which enables air-fuel-ratio feedback control to be quickly performed after startup of an internal combustion engine.

Patent Documents 1 and 2 disclose a technique for determining whether a linear sensor has entered a semi-activated state. A determination as to whether the air-fuel ratio is a rich-side air-fuel ratio or a lean-side air-fuel ratio can be performed on the basis of the sensor output, in a stage before the linear sensor has entered a fully activated state (completely activated state) after startup of the internal combustion engine. In this state, the sensor outputs a linear sensing output in accordance with the air-fuel ratio. These publications state that determination as to whether the air-fuel ratio is a rich-side air-fuel ratio or a lean-side air-fuel ratio is performed on the basis of a sensing output at the time the cell of the linear sensor is determined to have reached the semi-activated state.

[Patent Document 1] Japanese Patent Application Laid-Open (kokai) No. H9-170997

[Patent Document 2] Japanese Patent Application Laid-Open (kokai) No. 2004-69547

3. Problems To Be Solved By The Invention

From a different aspect, in addition to a limit-current-type sensor having a single cell disclosed in Patent Document 2, a layered-type gas sensor in which a pump cell and an oxygen-concentration measurement cell are layered is known as a linear sensor capable of detecting air-fuel ratio (oxygen concentration) over a wide range. More specifically, this layered-type gas sensor is configured such that pump and oxygen-concentration measurement cells each composed of a solid electrolytic layer and a pair of electrodes sandwiching the solid electrolytic layer are integrally layered. In this arrangement, one electrode of each cell is exposed to a measurement gas chamber, into which exhaust gas can be introduced via a diffusion control section.

For such a linear sensor composed of a plurality of cells, a technique for quickly starting air-fuel-ratio feedback control after startup of an internal combustion engine has been studied. In this technique, determination as to whether the air-fuel ratio is a rich-side air-fuel ratio or a lean-side air-fuel ratio is performed by use of an output of the sensor in a stage before the sensor reaches the fully activated state. A specific example thereof is a sensor control apparatus proposed in Japanese Patent Application No. 2005-264879, which had not yet been laid-open at the time of filing of this application. The sensor control apparatus determines whether a gas sensor (linear sensor) including a plurality of cells has reached a semi-activated state in a stage before the gas sensor reaches a fully activated state. After determining that the gas sensor cells have reached the semi-activated state, the sensor control apparatus determines whether the air-fuel ratio is on the rich side or the lean side on the basis of a voltage generated between the electrodes of one of the cells (e.g., an oxygen concentration measurement cell).

However, through keen studies, the present inventors found that, after the gas sensor including a plurality of cells has reached a semi-activated state, the voltage generated between the electrodes of the oxygen concentration measurement cell changes with delay in relation to an actual change in the air-fuel ratio, and the responsiveness of sensing output is not satisfactory. This phenomenon is considered to occur because exhaust gas introduced into the measurement gas chamber must pass through a diffusion control section, and replacement of gas in the measurement gas chamber occurs slowly because of the presence of the diffusion control section. Accordingly, the sensor control apparatus described in the prior application can carryout feedback control from a stage before the gas sensor has entered a fully activated state after startup of the sensor control apparatus. However, in order to perform accurate air-fuel-ratio feedback control in consideration of further rigorous strengthened emission control stands, the sensor control apparatus must have enhanced responsiveness, to changes in air-fuel ratio, of the sensing output generated once the gas sensor has reached the semi-activated state.

SUMMARY OF THE INVENTION

The present invention has been accomplished in view of the foregoing problems, and an object thereof is to provide an air-fuel ratio detection apparatus which enables a highly responsive sensing output for a change in air-fuel ratio to be obtained in a stage before a gas sensor reaches a fully activated state. The gas sensor includes a pump cell and an oxygen-concentration measurement cell layered such that one electrode of each cell is exposed to a hollow measurement gas chamber, into which exhaust gas can be introduced via a diffusion control section.

The above object of the invention has been achieved by providing an air-fuel ratio detection apparatus comprising a gas sensor. The gas sensor comprises a pump cell including a first solid electrolyte layer sandwiched between an outer pump electrode and an inner pump electrode and an oxygen concentration measurement cell including a second solid electrolyte layer sandwiched between a measurement electrode and a reference electrode. The pump cell and the oxygen concentration measurement cell are integrally layered such that the inner pump electrode and the measurement electrode face a (hollow) measurement gas chamber into which exhaust gas is introduced via a diffusion control section, and the inner pump electrode and the measurement electrode are maintained at the same potential. When the gas sensor is in a fully activated state, current is supplied to the pump cell so as to pump oxygen into or out of the measurement gas chamber such that a constant voltage is generated between the measurement electrode and the reference electrode of the oxygen concentration measurement cell. In this manner, the air-fuel ratio of exhaust gas can be detected over a wide range on the basis of the current flowing through the pump cell. The air-fuel ratio detection apparatus is characterized as comprising detection value acquisition means for acquiring, in a stage after startup of the air-fuel ratio detection apparatus and before the gas sensor reaches a fully activated state, a potential difference between the outer pump electrode of the pump cell and the reference electrode of the oxygen concentration measurement cell as a detection value; and rich-lean determination means for determining whether the air-fuel ratio of exhaust gas is on a rich side or a lean side for comparing the detection value with a predetermined air-fuel ratio threshold.

In the gas sensor having the above-described configuration, even in a stage preliminary to a fully activated state, an electromotive force (voltage) is generated between the pair of electrodes of the pump cell and between the pair of electrodes of the oxygen concentration measurement cell. The electromotive force is proportional to the difference in oxygen concentration between the opposite surfaces of each cell, providing that the gas sensor is heated to a certain temperature or higher.

In the air-fuel ratio detection apparatus of the present invention, since the inner pump electrode of the pump cell and the measurement electrode of the oxygen concentration measurement cell both face the measurement gas chamber, they are exposed to the same atmosphere. Further, the inner pump electrode and the measurement electrode are maintained at the same potential. This configuration can attain a potential (voltage) corresponding to a difference in oxygen concentration between the outer pump electrode and the reference electrode by measuring the potential difference between the outer pump electrode of the pump cell and the reference electrode of the oxygen concentration measurement cell.

Since the outer pump electrode is located on the side of the pump cell which does not face the measurement gas chamber to which exhaust gas is introduced via the diffusion control section, exhaust gas present outside the sensor reaches the outer pump electrode more easily than it reaches the electrodes facing the measurement gas chamber. In some cases, a porous electrode protection layer may be disposed on the outer pump electrode to prevent poisoning. However, in the present invention, even when such an electrode protection layer is provided, exhaust gas reaches the outer pump electrode more easily than it reaches the electrodes facing the measurement gas chamber. This is because the gas permeability of the electrode protection layer is set higher than that of the diffusion control section, in consideration of the configuration in which oxygen is pumped into or out of the measurement gas chamber when the gas sensor is in a fully activated state.

Therefore, a change in air-fuel ratio (change in atmosphere) can be detected more easily on the basis of the potential difference between the outer pump electrode and the reference electrode, as compared with the case where a change in air-fuel ratio is detected on the basis of the voltage generated between the electrodes of the oxygen concentration measurement cell. In the present invention, since the above-described potential difference is obtained, a sensing output highly responsive to a change in air-fuel ratio can be obtained. Thus, a determination as to whether the air-fuel ratio of exhaust gas is on the rich side or the lean side can be performed accurately by acquiring the potential difference between the outer pump electrode of the pump cell and the reference electrode of the oxygen concentration measurement cell as a detection value, and determining whether the air-fuel ratio of exhaust gas is on the rich side or the lean side based on the detection value.

Accordingly, the air-fuel ratio detection apparatus of the present invention can accurately determine whether the air-fuel ratio of exhaust gas is on the rich side or the lean side in a stage before the gas sensor reaches a fully activated state, and can perform accurate air-fuel-ratio feedback control in a preliminary stage before the gas sensor reaches a fully activated state.

From a different aspect, when the detection value acquisition means acquires the potential difference between the outer pump electrode of the pump cell and the reference electrode of the oxygen concentration measurement cell as a detection value, the gas sensor (in other words, the pump cell and the oxygen concentration measurement cell) must be heated to a certain temperature or higher such that an electromotive force is generated between the electrodes of each cell. Therefore, after a certain period of time has elapsed after startup of the air-fuel ratio detection apparatus, each cell is assumed to be in an activated state to some extent, and the detection value is acquired by means of the detection value acquisition means. However, the speed at which the gas sensor approaches the activated state varies depending on the environment to which the gas sensor is exposed, and even when a structure in which the gas sensor is heated by use of a heater is employed, the speed of approaching the activated state may vary because of the influence of a change in heater supply voltage.

In view of the above, preferably, the air-fuel ratio detection apparatus further comprises (i) semi-activation determination means for determining whether or not, after startup of the air-fuel ratio detection apparatus, the gas sensor has reached a semi-activated state in which a determination can be made as to whether or not the air-fuel ratio of exhaust gas is on the rich side or the lean side based on a change in the detection value, and (ii) full-activation determination means for determining whether or not the gas sensor has reached the fully activated state, wherein the detection value acquisition means acquires the detection value when the semi-activation determination means determines that the gas sensor has reached the semi-activated state and when the full activation determination means determines that the gas sensor has not yet reached the fully activated state.

According to the air-fuel ratio detection apparatus of the present invention, the detection value is acquired by means of the detection value acquisition means after the semi-activation determination means determines that the gas sensor has reached the semi-activated state and up until the time that the full activation determination means determines that the gas sensor has reached the fully activated state. That is, the acquisition of the detection value begins after the semi-activation determination means determines that the pump cell and the oxygen concentration measurement cell have been heated to a certain temperature or higher, and that these cells have reached an activated state in which an electromotive force corresponding to an oxygen concentration difference is generated between the electrodes of each cell. Therefore, the rich-lean determination means can reliably perform the determination by use of the detection value at a semi-activated stage preliminary to the fully activated stage.

The semi-activation determination means for determining whether the gas sensor has reached the semi-activated state may be means for energizing a heater attached to the gas sensor generally synchronized with startup of the air-fuel ratio detection apparatus, calculating cumulative electrical power supplied to the heater, and determining that the gas sensor has reached the semi-activated state when the cumulative electrical power reaches a preset reference value. However, in order to accurately determine whether or not the gas sensor has reached the semi-activated state, direct use of outputs obtained from the gas sensor is desirable.

In view of the above, preferably, the air-fuel ratio detection apparatus of the present invention further comprises a current source capable of supplying a constant current of a certain level to the oxygen concentration measurement cell; a constant-current-supply control section which alternately enters on and off states at predetermined intervals in order to alternately enable the current source to supply the constant current and disable the current source from supplying the constant current; voltage detection means for detecting a voltage generated between the measurement electrode and the reference electrode of the oxygen concentration measurement cell when the constant-current-supply control section is in the on state, and when the constant-current-supply control section is in the off state; and difference voltage detection means for detecting a difference voltage, which is the difference between the voltage detected by means of the voltage detection means when the constant-current-supply control section is in the on state and that detected when the constant-current-supply control section is in the off state, wherein the semi-activation determination means compares the difference voltage detected by means of the difference voltage detection means with a preset voltage judgment threshold, and determines that the gas sensor has reached the semi-activated state when the difference voltage becomes less than the voltage judgment threshold.

In the air-fuel ratio detection apparatus of the present invention, the difference voltage, which is the difference between the voltage detected when the current source is on and that detected when the current source is off, is detected, and a determination is made as to whether or not the gas sensor has reached the semi-activated state by comparing the difference voltage and the preset voltage judgment threshold. Since the determination as to whether or not the gas sensor has reached the semi-activated state is performed by direct detection of outputs from the gas sensor (specifically, the oxygen concentration measurement cell), the semi-activated state, which occurs during transition of the gas sensor from the non-activated state to the fully activated state, can be accurately detected.

Preferably, in the above-described air-fuel ratio detection apparatus, a shield layer for shielding the reference electrode of the oxygen concentration measurement cell from the outside environment is laminated on a side of the gas sensor where the reference electrode is provided. Also, the air-fuel ratio detection apparatus further comprises a reference-source-generation-current control section for causing the constant current to flow from the current source to the oxygen concentration measurement cell in a direction for pumping oxygen from the measurement gas chamber to the reference electrode, to thereby cause the reference electrode, shielded by means of the shield layer, to function as an internal oxygen reference source.

In the air-fuel ratio detection apparatus of the present invention, a common current source is used for two purposes; namely, for supplying a constant current to the oxygen concentration measurement cell so as to accumulate oxygen of a predetermined concentration at the reference electrode of the oxygen concentration measurement cell to thereby allow the reference electrode to function as an internal oxygen reference source, and for supplying a constant current to the oxygen concentration measurement cell so as to determine whether or not the gas sensor is in the semi-activated state. In this manner, both tasks of driving the gas sensor and determining whether or not the sensor is in a semi-activated state can be performed without the necessity of providing a plurality of current sources, whereby the cost of the air-fuel ratio detection apparatus can be lowered.

Preferably, the above-described air-fuel ratio detection apparatus further comprises element-resistance detection means for detecting an internal resistance of the pump cell or the oxygen concentration measurement cell, wherein the full activation determination means determines that the gas sensor has reached the fully activated state when the internal resistance detected by means of the element-resistance detection means becomes lower than a preset resistance judgment threshold.

In the case where the internal resistance of the pump cell or the oxygen concentration measurement cell is detected, the determination as to whether or not the gas sensor has reached the fully activated state can be performed accurately.

DESCRIPTION OF REFERENCE NUMERALS

Figure 1:
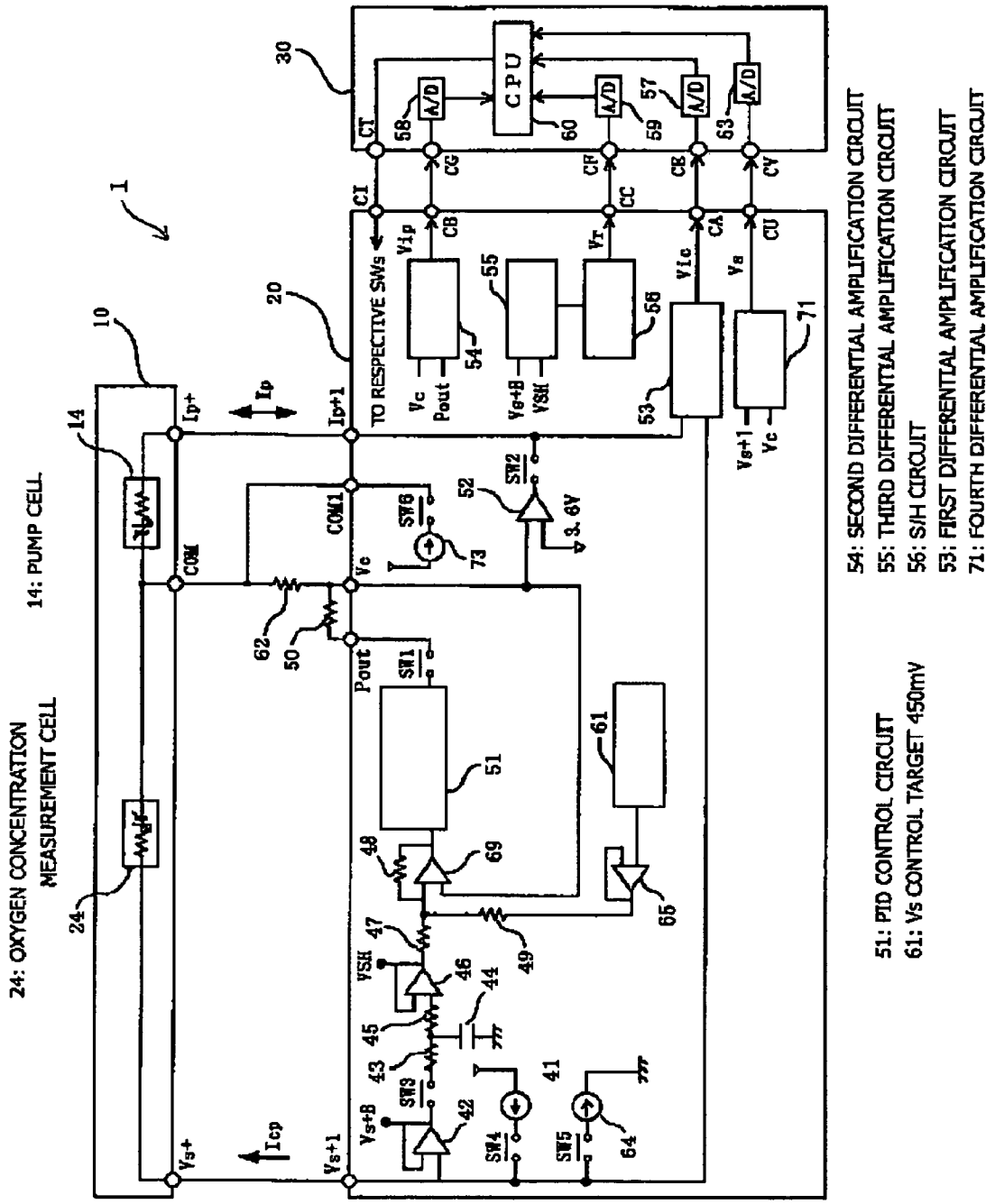
FIG. 1 is a circuit block diagram schematically showing the configuration of an air-fuel ratio detection apparatus.

Reference numerals used to identify various structural features shown in the drawings including the following.

1 . . . air-fuel ratio detection apparatus; 10 . . . full-range air-fuel ratio sensor (gas sensor); 12 . . . outer pump electrode; 13 . . . second solid electrolyte layer; 14 . . . pump cell; 15 . . . first solid electrolyte layer; 16 . . . inner pump electrode; 18 . . . diffusion control layer; 20 . . . sensor control circuit; 21 . . . measurement gas chamber; 22 . . . measurement electrode; 24 . . . oxygen concentration measurement cell;

28 . . . reference electrode; 30 . . . micro computer; 31 . . . shield layer; 32 . . . oxygen reference chamber; 41 . . . first current source; 50 . . . detection resistor; 51 . . . PID control circuit; 53 . . . first differential amplification circuit; 54 . . . second differential amplification circuit; 55 . . . third differential amplification circuit; 56 . . . signal hold circuit; 57 . . . first A/D conversion circuit; 58 . . . second A/D conversion circuit; 59 . . . third A/D conversion circuit; 60 . . . CPU; 63 . . . fourth A/D conversion circuit; 71 . . . fourth differential amplification circuit.

DETAILED DESCRIPTION OF THE PREFERRED EMBODIMENTS

A preferred embodiment of the present invention will be described below with reference to the drawings. However, the present invention shall not be construed as being limited thereto.

FIG. 1 is a circuit block diagram of an air-fuel ratio detection apparatus 1 equipped with a two-cell-type, full-range air-fuel ratio sensor 10 including a pump cell 14 and an oxygen concentration measurement cell 24.

As shown in FIG. 1, the air-fuel ratio detection apparatus 1, which detects air-fuel ratio of exhaust gas discharged from an internal combustion engine such as a gasoline engine or a diesel engine, includes the full-range air-fuel ratio sensor 10; a sensor control circuit 20 for driving and controlling the full-range air-fuel ratio sensor 10 and for outputting an output signal corresponding to the air-fuel ratio; and a microcomputer 30 for detecting the air-fuel ratio on the basis of the output signal and for controlling the internal combustion engine (specifically, controlling the injection quantity of fuel). Terminals Ip+1, COM1, Vs+1 of the sensor control circuit 20 are connected to the full-range air-fuel ratio sensor 10. Notably, terminals of the full-range air-fuel ratio sensor 10, to which the above-described terminals of the sensor control circuit 20 are connected, will be described below. Terminals CA, CB, CC, CI, and CU of the sensor control circuit 20 are connected to terminals CE, CG, CF, CT, and CV of the microcomputer 30.

Figure 2:
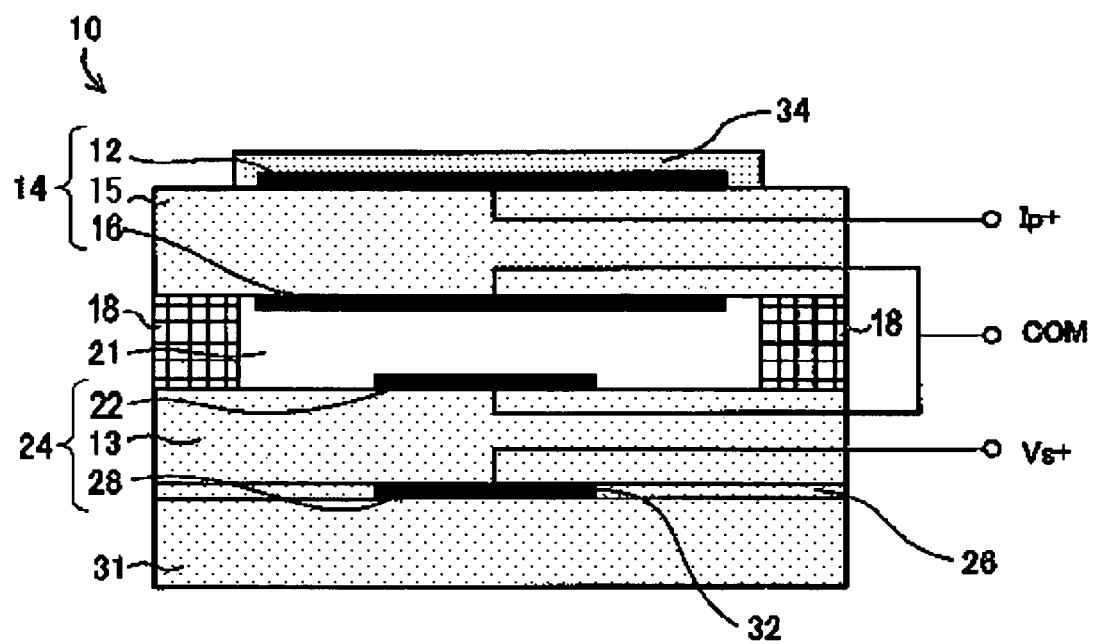
FIG. 2 is a view schematically showing the configuration of a full-range air-fuel ratio sensor (gas sensor) which constitutes the air-fuel ratio detection apparatus.

As shown in FIG. 2, the full-range air-fuel ratio sensor 10 includes the pump cell 14, which includes a first solid electrolyte layer 15 sandwiched between an outer pump electrode 12 and an inner pump electrode 16; the oxygen concentration measurement cell 24, which includes a second solid electrolyte layer 13 sandwiched between a measurement electrode 22 and a reference electrode 28; a hollow measurement gas chamber 21, which is provided between the pump cell 14 and the oxygen concentration measurement cell 24 and into which exhaust gas is introduced; a porous diffusion control layer 18 for introducing exhaust gas into the measurement gas chamber 21; and a shield layer 31, which is layered, via an insulating layer 26, on a surface of the oxygen concentration measurement cell 24 where the reference electrode 28 is provided so as to form an oxygen reference chamber 32 for accumulating oxygen between the shield layer 31 and the oxygen concentration measurement cell 24. Further, a porous electrode protection layer 34 is provided on the outer surface of the pump cell 14 in order to prevent poisoning of the outer pump electrode 12. Notably, the porosity and thickness of the electrode protection layer 34 are properly adjusted such that the electrode protection layer 34 exhibits higher gas permeability than does the diffusion control layer 18.

The inner pump electrode 16 of the pump cell 14 and the measurement electrode 22 of the oxygen concentration measurement cell 24 are disposed to face the measurement gas chamber 21. Each of the first solid electrolyte layer 15, the second solid electrolyte layer 13, and the shield layer 31 is mainly formed of zirconia partially stabilized with yttria. Each of the outer pump electrode 12, the inner pump electrode 16, the measurement electrode 22, and the reference electrode 28 is mainly formed of platinum. The measurement gas chamber 21 is a hollow portion formed by partially removing an insulating layer (not shown) mainly formed of alumina and disposed between the pump cell 14 and the oxygen concentration measurement cell 24. A portion of the insulating layer is cut and removed so as to form a channel for establishing communication between the hollow portion and the outside space, and the diffusion control layer 18, which is mainly formed of alumina, is provided in the channel.

The inner pump electrode 16 of the pump cell 14 and the measurement electrode 22 of the oxygen concentration measurement cell 24 are mutually connected, and are connected to an output terminal COM of the full-range air-fuel ratio sensor 10. That is, the inner pump electrode 16 and the measurement electrode 22 assume the same potential. The output terminal COM is connected to the terminal COM1 of the sensor control circuit 20 (see FIG. 1). Notably, as shown in FIG. 1, the inner pump electrode 16 and the measurement electrode 22 are connected not only to the terminal COM1, but also to a terminal Vc of the sensor control circuit 20 via a common wiring line. Further, the outer pump electrode 12 of the pump cell 14 is connected to an output terminal Ip+ of the full-range air-fuel ratio sensor 10, and the reference electrode 28 of the oxygen concentration measurement cell 24 is connected to the output terminal Vs+ of the full-range air-fuel ratio sensor 10. These output terminals Ip+ and Vs+ are connected to the terminals Ip+1 and Vs+1 of the sensor control circuit 20, respectively.

As shown in FIG. 1, the microcomputer 30 includes a first A/D conversion circuit 57, a second A/D conversion circuit 58, a third A/D conversion circuit 59, a fourth A/D conversion circuit 63, and a CPU 60. These AD conversion circuits 57, 58, 59, and 63 receive output signals from the sensor control circuit 20 via the terminals CE, CG, CF, and CV of the microcomputer 30, and outputs them to the CPU 60 after converting them into digital values. On the basis of the digitized output signals of the sensor control circuit 20, the CPU 60 calculates an air-fuel ratio or the internal resistance of the oxygen concentration measurement cell 24 or the like. As will be described below, the microcomputer 30 (specifically, the CPU 60) also outputs via the terminal CT to the terminal CI of the sensor control circuit 20 switching signals for turning on and off switches SW1 to SW6 contained in the sensor control circuit 20.

Next, the configuration and operation of the sensor control circuit 20 will be described by reference to FIG. 1. Notably, a major portion of the sensor control circuit 20 is realized by an application specific integrated circuit (ASIC).

The sensor control circuit 20 includes an operational amplifier 52 for supplying pump current Ip to the pump cell 14; a PID control circuit 51 for improving control characteristics of the pump current Ip; a first current source 41 for supplying very small current Icp to the oxygen concentration measurement cell 24 so as to maintain a constant oxygen concentration at the reference electrode 28 of the oxygen concentration measurement cell 24 (in other words, the oxygen concentration at the oxygen reference chamber 32); a constant voltage source 61 for supplying a voltage which serves as a control target for controlling the pump current Ip; and a detection resistor 50 whose opposite ends are connected to terminals Vc and Pout, respectively, and converts the pump current Ip flowing through the pump cell 14 to a voltage. The sensor control circuit 20 further includes a first differential amplification circuit 53 for amplifying, at a predetermined amplification factor, a differential voltage which is the difference between the potential at the terminal Ip+1 and the potential at the terminal Vs+1, and for outputting the result as a gas detection signal Vic; and a second differential amplification circuit 54 for amplifying, at a predetermined amplification factor, a voltage across the detection resistor 50 (the difference between the potential at the terminal Vc and the potential at the terminal Pout), and for outputting the result as a gas detection signal Vip. Moreover, the sensor control circuit 20 includes a fourth differential amplification circuit 71 for amplifying, at a predetermined amplification factor, a differential voltage which is the difference between the potential at the terminal Vs+1 and the potential at the terminal Vc, and for outputting the voltage Vs generated between the electrodes of the oxygen concentration measurement cell 24. Notably, since the first differential amplification circuit 53, the second differential amplification circuit 54, and the fourth differential amplification circuit 71 each have a known circuit configuration composed of an operational amplifier and resistors, they are depicted in the form of blocks in FIG. 1.

The first current source 41, the switch SW4, the oxygen concentration measurement cell 24, and a resistor 62 are connected in this sequence so as to form a current path for supplying a very small constant current Icp (e.g., 16 μA) to the oxygen concentration measurement cell 24 when the switch SW4 is on. When the very small current Icp flows through the oxygen concentration measurement cell 24 in a direction such that oxygen within the measurement gas chamber 21 is pumped to the reference electrode 28 side, the oxygen reference chamber 32 serves as an internal oxygen reference source.

The PID control circuit 51 has a known circuit configuration composed of a plurality of resistors and capacitors, which determine the control characteristic of the PID control circuit 51, operational amplifiers, etc. One end (input side) of the PID control circuit 51 is connected to the terminal Vs+1 via a differential amplification circuit composed of a first buffer 42, the switch SW3, resistors 43 and 45, a second buffer 46, resistors 47 and 48, and an operational amplifier 69. The other end (output side) of the PID control circuit 51 is connected to the terminal Pout via the switch SW1. Notably, the inverted input terminal of the operational amplifier 69, which is disposed in a stage before the PID control circuit 51 and forms a differential amplification circuit, is connected to the connection point between the resistors 47 and 49, and the non-inverted input terminal of the operational amplifier 69 is connected to the terminal Vc via an unillustrated resistor. The constant voltage source 61 supplies a voltage (450 mV), which serves as a control target for controlling the pump current, to the inverted input terminal of the operational amplifier 69 via a third buffer 65 and the resistor 49. Further, the output of the PID control circuit 51 is connected to the inverted input terminal of the operational amplifier 52 via the detection resistor 50; a reference voltage of 3.6 V is applied to the non-inverted input terminal of the operational amplifier 52; and the output terminal of the operational amplifier 52 is connected to the terminal Ip+1 via the switch SW2.

Operation of the sensor control circuit 20 for measuring oxygen concentration (air-fuel ratio) over a wide range will be described for the case where the full-range air-fuel ratio sensor 10 is in a fully activated state.

When the full-range air-fuel ratio sensor 10 reaches the fully activated state, the switches SW1 to SW4 are turned on, so that a very small current Icp flows from the first current source 41 to the oxygen concentration measurement cell 24. The PID control circuit 51 receives the output from the output terminal of the operational amplifier 69 and controls the magnitude of the pump current Ip by means of PID control such that the voltage Vs generated across the oxygen concentration measurement cell 24 becomes 450 mV. Specifically, through PID processing, the PID control circuit 51 calculates a deviation ΔVs of the voltage Vs generated across the oxygen concentration measurement cell 24 from the control target voltage 450 mV, and the deviation ΔVs is fed back to the operational amplifier 52 via the detection resistor 50, whereby the pump current Ip flows between the electrodes of the pump cell 14, and oxygen is pumped out of or into the measurement gas chamber 21 (see FIG. 2).

Since the magnitude and flow direction of the pump current Ip change in accordance with the air-fuel ratio (oxygen concentration) of exhaust gas, the concentration of oxygen in the exhaust gas can be detected over a wide range on the basis of the pump current Ip. Notably, the pump current Ip changes generally in proportion to the air-fuel ratio (oxygen concentration) of the exhaust gas. Specifically, since the detection resistor 50 is interposed in the current path through which the pump current Ip flows, a detection voltage corresponding to the magnitude of the pump current Ip is generated between the opposite ends of the detection resistor 50. In view of this, potentials at the opposite ends of the detection resistor 50 (specifically, the potential at the terminal Vc and the potential at the terminal Pout) are differential-amplified by means of the second differential amplification circuit 54, and the amplified potential difference is output via the terminal CB to the microcomputer 30 as a gas detection signal Vip. The gas detection signal Vip, output from the terminal CB of the sensor control circuit 20, is supplied to the terminal CG of the microcomputer 30, and is converted to a digital value by means of the second A/D conversion circuit 58. The digital value is processed by means of the CPU 60, whereby the air-fuel ratio is detected. The air-fuel ratio detected by means of the CPU 60 is fed back to fuel injection quantity, whereby air-fuel-ratio feedback control is performed.

The above description is for the case where the full-range air-fuel ratio sensor 10 is in the fully activated state; that is, in an ordinary state. In actuality, the above-described air-fuel-ratio feedback control making use of the gas detection signal Vip cannot be performed unless the full-range air-fuel ratio sensor 10 is sufficiently heated. In view of the foregoing, in order to eliminate the state where the air-fuel-ratio feedback control cannot be performed, the air-fuel ratio detection apparatus 1 of the present embodiment includes a processing system capable of determining whether the air-fuel ratio of exhaust gas is on the rich side or the lean side in relation to the theoretical air-fuel ratio, in a stage before the full-range air-fuel ratio sensor 10 reaches the fully activated state. When information as to whether exhaust gas is rich or lean is acquired in a stage before the full-range air-fuel ratio sensor 10 reaches the fully activated state and is used for the air-fuel-ratio feedback control, the air-fuel-ratio feedback control can be quickly started after startup of the internal combustion engine. Notably, in the present embodiment, the determination as to whether the air-fuel ratio of exhaust gas is on the rich side or the lean side is performed on the basis of the gas detection signal Vic, which is output from the first differential amplification circuit 53 provided in the sensor control circuit 20 and obtained by amplifying the difference between the potential at the terminal Vs+1 and that at the terminal Ip+1 at a predetermined amplification factor. This will be described in more detail below.

The air-fuel ratio detection apparatus 1 of the present embodiment also includes a processing system for measuring the internal resistance of the oxygen concentration measurement cell 24.

As shown in FIG. 1, in the sensor control circuit 20, the second buffer 46 forms a sample and hold circuit in cooperation with the switch SW3 and a capacitor 44. In a state in which the switch SW4 is turned on and the very small current Icp flows through the oxygen concentration measurement cell 24, when the switch SW3 is turned off, the sample and hold circuit holds the voltage Vs generated across the oxygen concentration measurement cell 24 immediately before supply of current for measuring the internal resistance of the oxygen concentration measurement cell 24.

When the switch SW3 is turned off, the switches SW5 and SW6 are turned on, whereby current having a predetermined magnitude for resistance measurement is supplied from the second current source 64 and the third current source 73 to the oxygen concentration measurement cell 24. A third differential amplification circuit 55 amplifies, at a predetermined amplification factor, the difference between the hold value VSH held by means of the second buffer 46 (the voltage Vs generated across the oxygen concentration measurement cell 24 immediately before supply of current for resistance measurement) and a potential Vs+B when the current for resistance measurement is supplied to the oxygen concentration measurement cell 24. Since the amplified differential voltage output from the differential amplification circuit 55 is proportional to the internal resistance (bulk resistance) of the oxygen concentration measurement cell 24, the amplified differential voltage can be used as a resistance signal Vrpvs. The voltage output from the third differential amplification circuit 55 is supplied to a signal hold circuit 56. Since the third differential amplification circuit 55 has a known circuit configuration composed of an operational amplifier and resistors, it is depicted in the form of a block in FIG. 1.

The signal hold circuit 56 has a known circuit configuration composed of a capacitor and a switch. When the switch provided in the signal hold circuit 56 is turned on, the signal hold circuit 56 starts its operation of holding the peak of the voltage output from the third differential amplification circuit 55. When the switch is turned off after elapse of a predetermined period of time after the switch has been turned on, the signal hold circuit 56 holds the peak of the voltage output from the third differential amplification circuit 55 as a resistance signal Vr, and outputs the held resistance signal Vr to the terminal CC.

The resistance signal Vr output from the terminal CC is supplied to the third A/D conversion circuit 59 via the terminal CF of the microcomputer 30, and is converted to a digital value. The digital value is processed by means of the CPU 60, whereby the internal resistance of the oxygen concentration measurement cell 24 is detected, and is compared with a preset resistance judgment threshold so as to determine whether the full-range air-fuel ratio sensor 10 has reached the fully activated state. The details of the processing in the microcomputer 30 will be described below.

Figure 3:
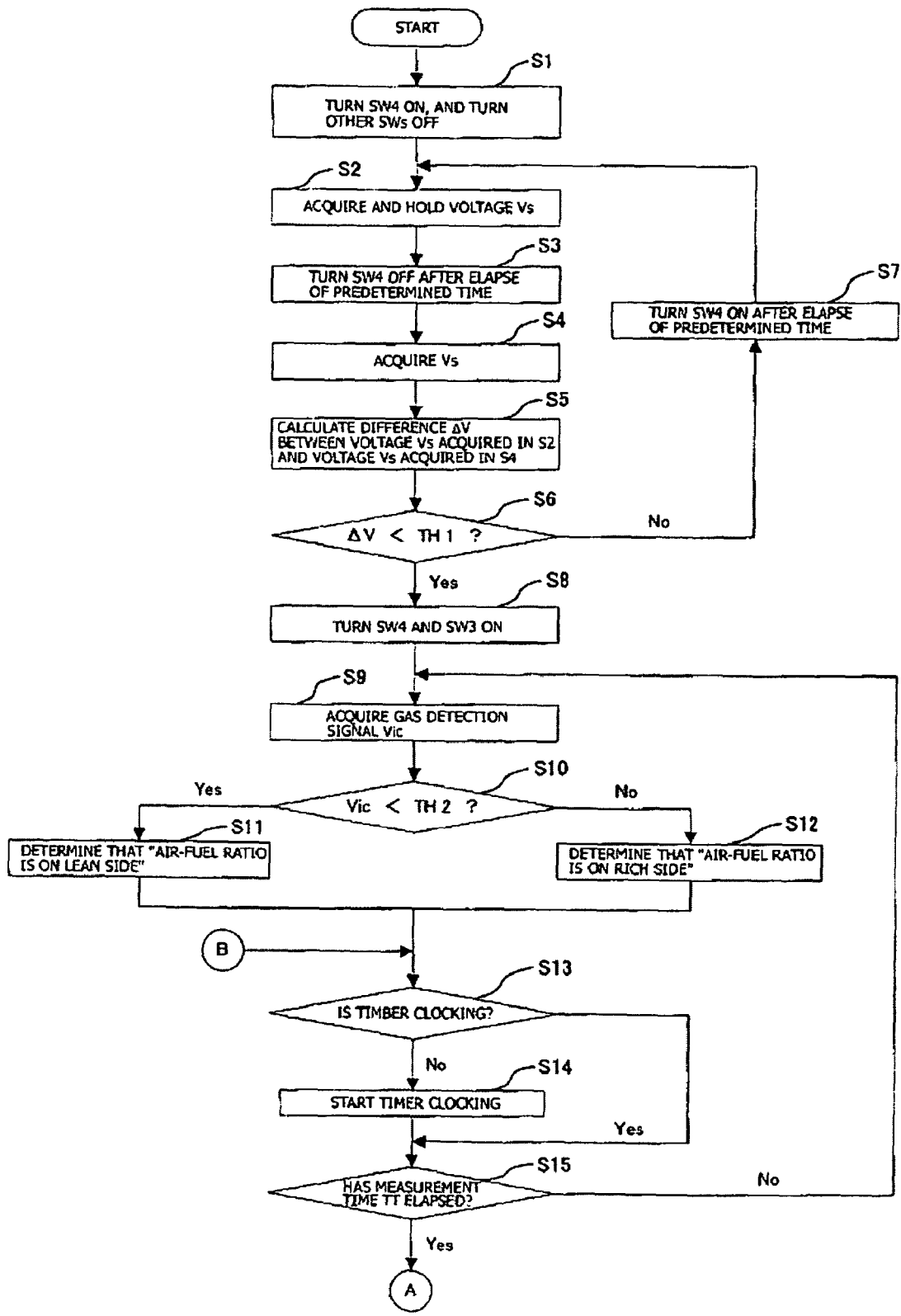
FIG. 3 is a flowchart representing the details of processing performed by the CPU of a micro computer which constitutes the air-fuel ratio detection apparatus.
Figure 4:
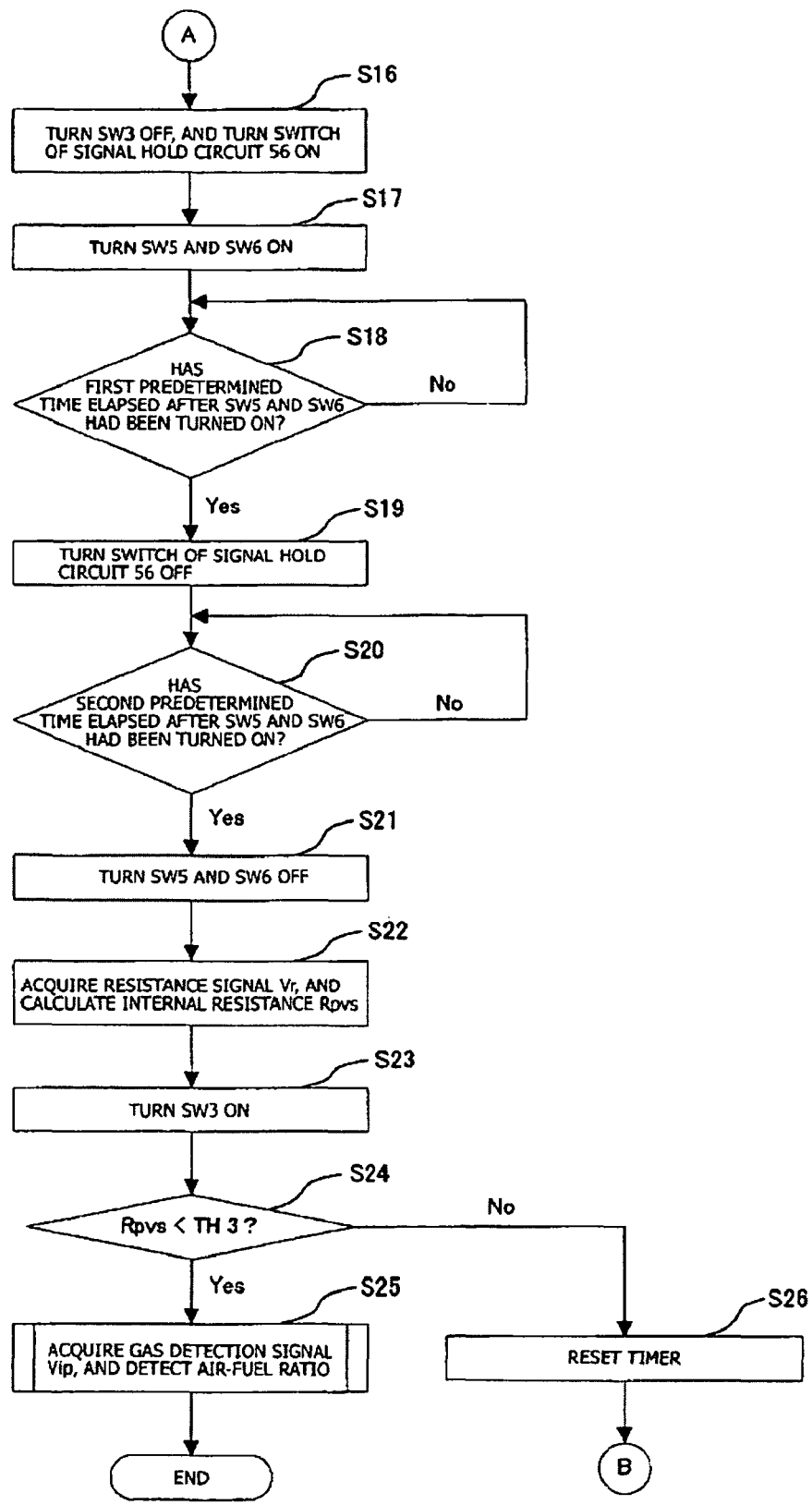
FIG. 4 is a flowchart representing the details of processing performed, after the processing of FIG. 3, by the CPU of the micro computer.

Next, the specific steps of a method of determining whether or not the air-fuel ratio of exhaust gas is on the rich side or the lean side in a stage before the full-range air-fuel ratio sensor 10 reaches the fully activated state and the specific steps of a method of determining whether or not the full-range air-fuel ratio sensor 10 has reached the fully activated state, which methods are performed in the air-fuel ratio detection apparatus 1 according to the present embodiment, will be described with reference to FIGS. 3 and 4. Notably, FIGS. 3 and 4 show the flow of software processing performed within the CPU 60 of the microcomputer 30, which partially constitutes the air-fuel ratio detection apparatus 1. The processing by the microcomputer 30 is started when the internal combustion engine is started by means of an ignition key.

As shown in FIG. 3, in S1 (S represents a step; this applies the steps described below), the CPU 60 first outputs via the terminal CT to the terminal CI of the sensor control circuit 20 switching signals for turning on the switch SW4 and for turning off the switches SW1 to SW3, SW5, and SW6, as well as the switch of the signal hold circuit 56. As result, a very small current Icp is supplied from the first current source 41 to the oxygen concentration measurement cell 24. In S2, the CPU 60 acquires the potential output from the fourth differential amplification circuit 71 and the terminal CU (that is, the voltage Vs generated between the electrodes of the oxygen concentration measurement cell 24). Specifically, in the microcomputer 30, the voltage input via the terminal CV is converted to a digital value by means of the fourth A/D conversion circuit 63, and the digital value is read by the CPU 60. Further, in S2, the voltage Vs converted to a digital value is held in memory (not shown in FIG. 1).

After elapse of a predetermined time in S3 (elapse of 50 msec in the above-described case of a 10 Hz switching operation having a duty ratio of 50%), the CPU 60 turns the switch SW4 off. The CPU 60 then proceeds to S4, and acquires the voltage Vs (that is, the voltage Vs generated between the electrodes of the oxygen concentration measurement cell 24) output via the fourth differential amplification circuit 71 and the terminal CU, as in S2. Further, in S5, the CPU 60 calculates a difference voltage ΔV between the voltage Vs held in the above-described S2 and the voltage Vs detected in S4.

The CPU 60 then proceeds to S6, and compares the difference voltage ΔV calculated in S5 and a preset voltage judgment threshold TH1. When in S6 the difference voltage ΔV is determined not to be less than the voltage judgment threshold TH1, the CPU 60 proceeds to S7, and turns the switch SW4 on after elapse of a predetermined time (50 msec), to thereby supply the very small current Icp to the oxygen concentration measurement cell 24. After that, the CPU 60 repeats S2 and steps subsequent thereto.

Meanwhile, when in S6 the difference voltage ΔV is determined to have become less than the voltage judgment threshold TH1, the CPU 60 determines that the full-range air-fuel ratio sensor 10 has reached a semi-activated state in which determination as to whether or not the air-fuel ratio of exhaust gas is on the rich side or the lean side can be performed on the basis of a change in the gas detection signal Vic output from the first differential amplification circuit 53. In this case, the CPU 60 proceeds to S8, and turns the switch SW4 on so as to supply the very small current Icp to the oxygen concentration measurement cell 24 and turns the switch SW3 on.

Subsequently, in S9, the CPU 60 acquires the gas detection voltage Vic output from the first differential amplification circuit 53; i.e., a voltage obtained as a result of amplification, at a predetermined amplification factor, of the difference between the potential at the terminal Ip+1 (i.e., the potential at the outer pump electrode 12 of the pump cell 14) and the potential at the terminal Vs+1 (i.e., the potential at the reference electrode 28 of the oxygen concentration measurement cell 24). Specifically, in the microcomputer 30, the voltage input via the terminal CE is converted into a digital value by means of the first A/D conversion circuit 57, and is read by the CPU 60.

The CPU 60 then proceeds to S10, and compares the acquired gas detection signal Vic and an air-fuel-ratio threshold TH2 corresponding to the theoretical air-fuel ratio. When in S10 the gas detection signal Vic is determined to be smaller than the air-fuel-ratio threshold TH2, the CPU 60 proceeds to S11 and determines that the "air-fuel ratio is on the lean side." Meanwhile, when the gas detection signal Vic is determined in S10 to be not smaller than the air-fuel-ratio threshold TH2, the CPU 60 proceeds to S12 and determines that the "air-fuel ratio is on the rich side."

The CPU 60 then proceeds to S13 and determines whether or not a timer, which will be mentioned in the next step S14, has already started a clocking operation. When in S13 the CPU 60 determines that the count value of the timer is zero and the clocking operation has not yet been started, in S14, the CPU 60 starts the clocking operation by means of the timer, and then proceeds to S15. Meanwhile, when in S13 the CPU 60 determines that the clocking has already been started, the CPU 60 proceeds to S15. In S15, the CPU 60 determines whether or not the timer has clocked a measurement time TT (e.g., 100 msec after start of the timer) for measuring the internal resistance of the oxygen concentration measurement cell 24. When the measurement time TT has not yet elapsed, the CPU 60 returns to S9, and repeats the processing of S9 and subsequent steps until a positive determination is made in S15. When in S15 the timer is determined to have clocked the measurement time TT, the CPU 60 proceeds to S16 shown in FIG. 4. In S16, the CPU 60 turns the switch SW3 off, and turns on the switch (not shown in FIG. 1) of the signal hold circuit 56. Subsequently, in S17, the CPU 60 turns the switches SW5 and SW6 on so as to supply a constant current for resistance measurement from the second current source 64 and the third current source 73 to the oxygen concentration measurement cell 24, and then proceeds to S18.

In S18, the CPU 60 determines whether or not a first predetermined time (e.g., 60 μsec) has elapsed after the switches SW5 and SW6 had been turned on. When the first predetermined time has not yet elapsed, the CPU 60 repeats the processing of S18. When the CPU 60 determines in S18 that the first predetermined time has elapsed, in S19 the CPU 60 turns the switch of the signal hold circuit 56 off. As a result, the signal hold circuit 56 holds the peak of the voltage output from the third differential amplification circuit at that time (a voltage obtained as a result of amplification, at a predetermined amplification factor, of the difference between the hold value VSH held by the second buffer 46 and the potential Vs+B at the time when the current for resistance measurement is supplied to the oxygen concentration measurement cell 24).

Subsequently, in S20, the CPU 60 determines whether or not a second predetermined time (e.g., 100 μsec) has elapsed after the switches SW5 and SW6 had been turned on. When the second predetermined time has not yet elapsed, the CPU 60 repeats the processing of S20. When the CPU 60 determines in S20 that the second predetermined time has elapsed, in S21, the CPU 60 turns the switches SW5 and SW6 off, and then proceeds to S22. In S22, the CPU 60 acquires the resistance signal Vr output from the signal hold circuit 56, and calculates the internal resistance Rpvs of the oxygen concentration measurement cell 24 on the basis of the voltage of the acquired resistance signal Vr and the current supplied from the second and third current sources 64 and 73. After that, the CPU 60 proceeds to S23 and turns the switch SW3 on.

The CPU 60 then proceeds to S24 and compares the internal resistance Rpvs detected in S22 with a preset resistance judgment threshold TH3 (e.g., 220Ω). When in S24 the internal resistance Rpvs is determined to be lower than the resistance judgment threshold TH3, the CPU 60 determines that the full-range air-fuel ratio sensor 10 has reached the fully activated state, and proceeds to S25. Meanwhile, when in S23 the internal resistance Rpvs is determined not to be lower than the resistance judgment threshold TH3, the CPU 60 determines that full-range air-fuel ratio sensor 10 has not yet reached a fully activated stage and proceeds to S26 so as to reset the clocked time of the timer; i.e., set the count value of the timer to zero, and then returns to S13 (see FIG. 3).

When the CPU 60 proceeds to S25, the CPU 60 starts the above-described ordinary operation for the case where the full-range air-fuel ratio sensor 10 has reached the fully activated state; such as turning the switches SW1 and SW2 on. With this, after this point in time, the air-fuel ratio (oxygen concentration) is detected over a wide range on the basis of the gas detection signal Vip output from the second differential amplification circuit 54 of the sensor control circuit 20, and proper air-fuel-ratio feedback control is performed on the basis of the detected air-fuel ratio. Notably, since the processing for the case where the full-range air-fuel ratio sensor 10 has reached the fully activated state has been described in detail above, its description is omitted from the description of the present flowchart. The processing of S25 is repeatedly executed until the internal combustion engine is stopped by means of an ignition key (in other words, until the air-fuel ratio detection apparatus 1 is stopped).

In the air-fuel ratio detection apparatus 1 of the present embodiment, the first differential amplification circuit 53, the first A/D conversion circuit 57, and the processing of S9 in the CPU 60 correspond to the detection value acquisition means, and the processing of S10 to S12 in the CPU 60 corresponds to the lean-rich detection means. The processing of S1 to S7 in the CPU 60 corresponds to the semi-activation determination means. Further, the processing of S1, S3, and S7 in the CPU 60 corresponds to the constant-current-supply control section; the fourth differential amplification circuit 71, the fourth A/D conversion circuit 63, and the processing of S2 and S4 in the CPU 60 correspond to the voltage detection means; and the processing of S5 corresponds to the difference voltage detection means. Moreover, the processing of S8 in the CPU 60 corresponds to the reference-source-generation-current control section; the third differential amplification circuit 55, the signal hold circuit 56, the third A/D conversion circuit 59, and the processing of S13 to S23 in the CPU 60 correspond to the element-resistance detection means; and the processing of S24 corresponds to the full activation determination means.

As described above, the air-fuel ratio detection apparatus 1 determines, on the basis of the difference voltage ΔV, whether or not after startup of the apparatus 1 the full-range air-fuel ratio sensor 10 has reached a semi-activated state in which a determination can be made as to whether or not the air-fuel ratio of exhaust gas is on the rich side or the lean side on the basis of a change in the gas detection signal Vic. When the full-range air-fuel ratio sensor 10 is determined to have reached the semi-activated state, the gas detection signal Vic is compared with the predetermined air-fuel ratio threshold TH2 so as to determine whether the air-fuel ratio of exhaust gas is on the rich side or the lean side. By virtue of this, air-fuel-ratio feedback control can be realized even before the full-range air-fuel ratio sensor 10 reaches the fully activated state.

Moreover, in the air-fuel ratio detection apparatus 1, after the full-range air-fuel ratio sensor 10 reaches the above-mentioned semi-activated state, the potential difference between the outer pump electrode 12 of the pump cell 14 and the reference electrode 28 of the oxygen concentration measurement cell 24 is obtained as the gas detection signal Vic via the first differential amplification circuit 53. The outer pump electrode 12 does not face the measurement gas chamber, into which exhaust gas is introduced via the diffusion control layer 18, and the electrode protection layer 34, which is provided on the outer pump electrode 12, has a higher gas permeability than the diffusion control layer 18. Therefore, exhaust gas reaches the outer pump electrode 12 more easily than it reaches the measurement gas chamber 21 via the diffusion control layer 28. Therefore, a change in air-fuel ratio (change in atmosphere) can be detected more easily on the basis of the potential difference between the outer pump electrode 12 and the reference electrode 28, as compared with the case where a change in air-fuel ratio is detected on the basis of the voltage generated between the electrodes of the oxygen concentration measurement cell 24. Accordingly, since the air-fuel ratio detection apparatus 1 acquires the above-described potential difference, a sensing output having a high responsiveness for a change in air-fuel ratio can be obtained, and determination as to whether the air-fuel ratio is on the rich side or the lean side can be performed accurately.

By virtue of the above-described features, the air-fuel ratio detection apparatus 1 of the present embodiment allows the internal combustion engine to perform accurate air-fuel-ratio feedback control from a stage before the full-range air-fuel ratio sensor 10 reaches the fully activated state.

Although an embodiment of the present invention has been described above, the present invention is not limited to this embodiment, and may assume any of various forms without departing from the technical scope of the present invention.

For example, in the embodiment, the first differential amplification circuit 53 is used in order to detect the potential difference between the outer pump electrode 12 of the pump cell 14 and the reference electrode 28 of the oxygen concentration measurement cell 24. However, a configuration may be employed in which the potential at the outer pump electrode 12 (the potential at the terminal Ip+1) and the potential at the reference electrode 28 (the potential at the terminal Vs+1) are individually supplied to the microcomputer 30, in which the CPU 60 of the micro computer 30 detects the difference between the two potentials as a detection value, and compares the detection value with the air-fuel ratio threshold TH2.

In the above-described embodiment, the porous diffusion control layer 18 is provided in order to introduce exhaust gas into the measurement gas chamber 21 of the full-range air-fuel ratio sensor 10 while controlling the flow rate of the exhaust gas. Instead of providing the diffusion control layer, a small hole may be provided in the insulating layer disposed between the pump cell 14 and the oxygen concentration measurement cell 24 so as to introduce exhaust gas into the measurement gas chamber 21 while controlling the flow rate of the exhaust gas.

Although not described in the above embodiment, a heater is attached to the full-range air-fuel ratio sensor 10 in order to quickly activate the full-range air-fuel ratio sensor 10. The embodiment may be modified to determine whether or not the full-range air-fuel ratio sensor 10 is in the fully activated state, by use of the heater. Specifically, after start of supply of voltage to the heater, the cumulative electrical power supplied to the heater is detected, and when the cumulative electrical power reaches a preset value, the full-range air-fuel ratio sensor 10 is determined to have reached the fully activated state.

This application is based on Japanese Patent Application JP 2005-342937, filed on Nov. 28, 2006, the entire contents of which are hereby incorporated by reference, the same as if set forth at length.

What is claimed is:

1. An air-fuel ratio detection apparatus comprising a gas sensor including:
  a measurement gas chamber into which exhaust gas is introduced via a diffusion control section;
  a pump cell including an outer pump electrode, an inner pump electrode facing the measurement gas chamber, and a first solid electrolyte layer sandwiched between the outer pump electrode and the inner pump electrode,
  an oxygen concentration measurement cell including a measurement electrode facing the measurement gas chamber and maintained at the same potential as the inner pump electrode, a reference electrode, and a second solid electrolyte layer sandwiched between the measurement electrode and the reference electrode, the pump cell being integrally laminated with the oxygen concentration measurement cell,
  means, when the gas sensor is in a fully activated state, for supplying current to the pump cell so as to pump oxygen into or out of the measurement gas chamber such that a constant voltage is generated between the measurement electrode and the reference electrode of the oxygen concentration measurement cell, and an air-fuel ratio of exhaust gas introduced into the measurement gas chamber is detectable based on current flowing through the pump cell,
  semi-activation determination means for determining whether or not, after startup of the air-fuel ratio detection apparatus, the gas sensor has reached a semi-activated state in which a determination can be made as to whether or not the air-fuel ratio of exhaust gas is on the rich side or the lean side based on a change in the detection value,
  full-activation determination means for determining whether or not the gas sensor has reached the fully activated state,
  a current source capable of supplying a constant current of a certain magnitude to the oxygen concentration measurement cell;
  a constant-current-supply control section which alternately enters on and off states at predetermined intervals in order to alternately enable the current source to supply the constant current and disable the current source from supplying the constant current;
  voltage detection means for detecting a voltage generated between the measurement electrode and the reference electrode of the oxygen concentration measurement cell when the constant-current-supply control section is in the on state, and when the constant-current-supply control section is in the off state;
  difference voltage detection means for detecting a difference voltage, which is the difference between the voltage detected by means of the voltage detection means when the constant-current-supply control section is in the on state and that detected when the constant-current-supply control section is in the off state, and
  element-resistance detection means for detecting an internal resistance of the pump cell or the oxygen concentration measurement cell,
  the air-fuel ratio detection apparatus further comprising:
  detection value acquisition means for acquiring, in a stage after startup of the air-fuel ratio detection apparatus and before the gas sensor reaches the fully activated state, a detection value which is a potential difference between the outer pump electrode of the pump cell and the reference electrode of the oxygen concentration measurement cell; and rich-lean determination means for determining whether the air-fuel ratio of exhaust gas is on a rich side or a lean side by comparing the detection value with a predetermined air-fuel ratio threshold, wherein the detection value acquisition means acquires the detection value when the semi-activation determination means determines that the gas sensor has reached the semi-activated state and when the full activation determination means determines that the gas sensor has not yet reached the fully activated state, the semi-activation determination means compares the difference voltage detected by means of the difference voltage detection means with a preset voltage judgment threshold, and determines that the gas sensor has reached the semi-activated state when the difference voltage becomes less than the voltage judgment threshold, and the full activation determination means determines that the gas sensor has reached the fully activated state when the internal resistance detected by means of the element-resistance detection means becomes lower than a preset resistance judgment threshold.

2. The air-fuel ratio detection apparatus according to claim 1, further comprising:

a shield layer for shielding the reference electrode of the oxygen concentration measurement cell external to the gas sensor, said shield layer being laminated on a side of the gas sensor where the reference electrode is provided; and a reference-source-generation-current control section for causing the constant current to flow from the current source to the oxygen concentration measurement cell in a direction for pumping oxygen from the measurement gas chamber to the reference electrode, to thereby cause the reference electrode, shielded by means of the shield layer, to function as an internal oxygen reference source.

3. An air-fuel ratio detection apparatus comprising a gas sensor including:

a measurement gas chamber into which exhaust gas is introduced via a diffusion control section;

a pump cell including an outer pump electrode, an inner pump electrode facing the measurement gas chamber, and a first solid electrolyte layer sandwiched between the outer pump electrode and the inner pump electrode, and an oxygen concentration measurement cell including a measurement electrode facing the measurement gas chamber and maintained at the same potential as the inner pump electrode, a reference electrode, and a second solid electrolyte layer sandwiched between the measurement electrode and the reference electrode, the pump cell being integrally laminated with the oxygen concentration measurement cell, wherein, when the gas sensor is in a fully activated state, current is supplied to the pump cell so as to pump oxygen into or out of the measurement gas chamber such that a constant voltage is generated between the measurement electrode and the reference electrode of the oxygen concentration measurement cell, and an air-fuel ratio of exhaust gas introduced into the measurement gas chamber is detectable based on current flowing through the pump cell, and means for determining, in a stage after startup of the air-fuel ratio detection apparatus and before the gas sensor reaches the fully activated state, whether the air-fuel ratio of exhaust gas is on a rich side or a lean side by comparing a detection value with a predetermined air-fuel ratio threshold, the detection value being a potential difference between the outer pump electrode of the pump cell and the reference electrode of the oxygen concentration measurement cell, semi-activation determination means for determining whether or not, after startup of the air-fuel ratio detection apparatus, the gas sensor has reached a semi-activated state in which a determination can be made as to whether or not the air-fuel ratio of exhaust gas is on the rich side or the lean side based on a change in the detection value, full-activation determination means for determining whether or not the gas sensor has reached the fully activated state, a current source capable of supplying a constant current of a certain magnitude to the oxygen concentration measurement cell;

a constant-current-supply control section which alternately enters on and off states at predetermined intervals in order to alternately enable the current source to supply the constant current and disable the current source from supplying the constant current;

voltage detection means for detecting a voltage generated between the measurement electrode and the reference electrode of the oxygen concentration measurement cell when the constant-current-supply control section is in the on state, and when the constant-current-supply control section is in the off state;

difference voltage detection means for detecting a difference voltage, which is the difference between the voltage detected by means of the voltage detection means when the constant-current-supply control section is in the on state and that detected when the constant-current-supply control section is in the off state, and element-resistance detection means for detecting an internal resistance of the pump cell or the oxygen concentration measurement cell, wherein a detection value acquisition means acquires the detection value when the semi-activation determination means determines that the gas sensor has reached the semi-activated state and when the full activation determination means determines that the gas sensor has not yet reached the fully activated state, the semi-activation determination means compares the difference voltage detected by means of the difference voltage detection means with a preset voltage judgment threshold, and determines that the gas sensor has reached the semi-activated state when the difference voltage becomes less than the voltage judgment threshold, and the full activation determination means determines that the gas sensor has reached the fully activated state when the internal resistance detected by means of the element-resistance detection means becomes lower than a preset resistance judgment threshold.

* * * * *